United States Patent [19]

Szczepanski

[11] Patent Number: 4,468,242
[45] Date of Patent: Aug. 28, 1984

[54] OXIME DERIVATIVES FOR PROMOTING THE GROWTH OF SOYBEANS

[75] Inventor: Henry Szczepanski, Rheinfelden, Switzerland

[73] Assignee: Ciba-Geigy Corporation, Ardsley, N.Y.

[21] Appl. No.: 238,345

[22] Filed: Feb. 26, 1981

Related U.S. Application Data

[62] Division of Ser. No. 69,414, Aug. 24, 1979, Pat. No. 4,269,775.

[51] Int. Cl.³ .................... A01N 43/26; A01N 43/32
[52] U.S. Cl. .................................. 71/88; 71/93; 71/100
[58] Field of Search .............. 71/76, 88, 105

[56] References Cited

U.S. PATENT DOCUMENTS

| | | | |
|---|---|---|---|
| 3,896,155 | 7/1975 | Hamprecht et al. | 260/465 E |
| 3,980,693 | 9/1976 | Kuble et al. | 260/465 E |
| 4,070,389 | 1/1978 | Martin | 71/105 |
| 4,152,137 | 5/1979 | Martin | 71/105 |

FOREIGN PATENT DOCUMENTS 515449  3/1978  Australia .

*Primary Examiner*—Catherine L. Mills
*Attorney, Agent, or Firm*—Frederick H. Rabin

[57] ABSTRACT

The invention relates to oximes of the formula

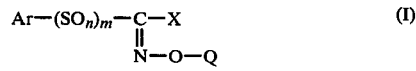

wherein n is 0, 1 or 2 and m is 0 or 1, and wherein Ar is a phenyl radical

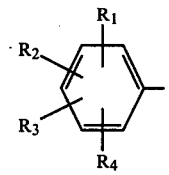

a naphthyl radical substituted by $R_2$ and $R_3$, a 5- to 10-membered heterocyclic radical which contains not more than 3 identical or different heteroatoms N, O and/or S, and which is substituted by $R_2$, $R_3$ and $R_4$ and can be substituted by oxo or thiono, or, if m is O, Ar is a radical R—CO—, wherein R is a radical —OR$_5$, and Q is a radical $C_aH_{2a}$—R$_8$, wherein a is an integer between 1 and 6, while R and $R_8$ are as defined in the description of the specification. These compounds can be used for protecting plant crops from the action of aggressive agrochemicals.

3 Claims, No Drawings

OXIME DERIVATIVES FOR PROMOTING THE GROWTH OF SOYBEANS

This is a division of application Ser. No. 069,414 filed on Aug. 24, 1979, now U.S. Pat. No. 4,269,775.

The present invention relates to a method of protecting plant crops from the phytotoxic action of potent herbicides by means of oxime derivatives and also to a number of novel oxime derivatives.

The oxime derivatives employed as active compounds have the formula I

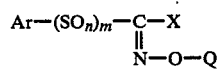  (I)

wherein
n is 0, 1 and 2 and m is 0 or 1, and
Ar is a phenyl radical

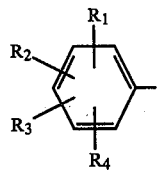

a naphthyl radical substituted by $R_2$ and $R_3$, a 5- to 10-membered heterocyclic radical which contains not more than 3 identical or different heteroatoms N, O and/or S and which is substituted by $R_2$, $R_3$ and $R_4$ and can be substituted by oxo or thiono, or if m is 0, Ar is a radical R—CO, wherein R is a radical —$OR_5$, in which $R_5$ is an aliphatic group containing not more than 8 carbon atoms or is an araliphatic group containing not more than 15 carbon atoms or is a cycloaliphatic or aromatic group, each containing not more than 10 carbon atoms, while the possible substituents of the aromatic radicals or of the cycloaliphatic radical are halogen, —CN, —$NO_2$, lower alkyl, lower alkoxy, haloalkyl; or R is a radical —NH—CO—NH—$R_7$ or a radical —N($R_6$)($R_7$), wherein $R_6$ is hydrogen or lower alkyl and $R_7$ is hydrogen or an aliphatic group containing not more than 8 carbon atoms or an araliphatic group containing not more than 15 carbon atoms, or a cycloaliphatic or aromatic group containing not more than 10 carbon atoms, while possible substituents of the aromatic groups or of the cycloaliphatic radical are halogen, —CN, $NO_2$, lower alkyl, lower alkoxy, or haloalkyl; or R is a radical —N($R_6$)($R_7$), wherein $R_6$ and $R_7$ together form a 5- or 6-membered heterocyclic ring which can additionally contain oxygen as possible further heteroatom, $R_1$ is hydrogen, halogen, lower alkyl, lower alkoxy or a p-phenoxy radical which is unsubstituted or at most disubstituted by halogen, CN, $NO_2$, $CF_3$, $R_2$, $R_3$ and $R_4$, each independently of the other, are hydrogen, halogen, CN, $NO_2$, lower alkyl, lower alkoxy, haloalkyl, haloalkoxy, lower alkanoyl, OH, phenyl, halophenyl, lower carbalkoxy, lower alkoxycarbonyl, lower alkoxycarbonyloxy, lower carbamoyloxy, lower alkylthio, lower alkylsulfonyl, phenalkoxy, cyclohexyl, $NH_2$, —NH-lower alkyl, —N(di-lower alkyl), lower alkanoylamino, carbamoyl, sulfamoyl, X is hydrogen, —CN, halogen, lower alkyl, lower alkanoyl, —COOH, a carboxylic acid ester radical, a carbamoyl radical, and Q is the radical —$C_aH_{2a}$—$R_8$, wherein a is an integer between 1 and 6, while the corresponding radical can also be branched and $R_8$ is one of the following radicals:

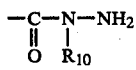

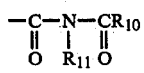

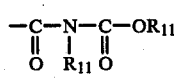

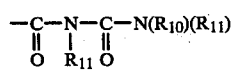

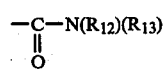

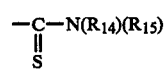

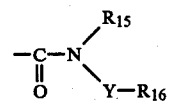

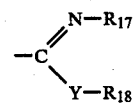

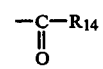

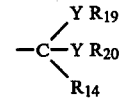

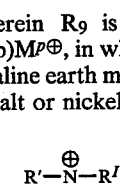

wherein $R_9$ is hydrogen or the cation of a base $(1/p)M^{p\oplus}$, in which M is the cation of an alkali metal or alkaline earth metal or an iron, copper, zinc, manganese, cobalt or nickel cation or an amino radical $$R'-\overset{\oplus}{\underset{R''}{N}}-R^{IV}\\R'''$$

and p is an integer 1, 2 or 3 which corresponds to the valency of the cation, while R', R", R''' and $R^{IV}$, each independently of the other, are hydrogen, benzyl or a $C_1$-$C_4$alkyl radical which is unsubstituted or substituted by —OH, —$NH_2$ or $C_1$-$C_4$alkoxy; $R_{10}$ is hydrogen, an aliphatic radical, an araliphatic radical or an aromatic radical which is unsubstituted or mono- or polysubstituted by halogen, haloalkyl, lower alkoxy and/or cyano; $R_{11}$ represents hydrogen or lower alkyl; $R_{12}$ and $R_{13}$ together with the nitrogen atom to which they are attached form a 5- to 6-membered ring which is unsubstituted or mono- or polysubstituted by halogen, cyano and/or lower alkyl and which can be interrupted by a nitrogen, oxygen or sulfur atom; $R_{14}$ is a cycloaliphatic, araliphatic or aliphatic radical or an aromatic radical which is unsubstituted or mono- or polysubstituted by halogen, haloalkyl, lower alkoxy and/or cyano; $R_{15}$ is hydrogen, lower alkyl or cycloalkyl; $R_{16}$ is an aliphatic radical which is substituted or substituted by cyano or an aromatic radical which is unsubstituted or mono- or polysubstituted by halogen, haloalkyl, lower alkoxy and/or cyano; $R_{17}$ is hydrogen, lower alkenyl or lower alkynyl which is unsubstituted or substituted by halogen, or is lower alkyl or cycloalkyl; $R_{18}$ is lower alkyl or cycloalkyl; $R_{17}$ and $R_{18}$ together with —N=C—Y— forms a 5- to 6-membered ring which is unsubstituted or substituted by lower alkyl; $R_{19}$ and $R_{20}$, each independently of the other, are lower alkyl or together with —Y—C—Y— form a 5- to 6-membered ring which is unsubstituted or substituted by lower alkyl, halogen and/or nitro, and Y is oxygen or sulfur.

By halogen in formula I is meant fluorine, chlorine, bromine or iodine.

Carboxylic acid esters are lower alkyl esters. Carbamoyl radicals, in addition to —CONH$_2$, are also monoalkyl-substituted or symmetrically or unsymmetrically dialkyl-substituted amides, in which the alkyl groups are lower alkyl groups.

The term alkyl by itself or as moiety of another substituent comprises branched or unbranched alkyl groups of 1 to 8 carbon atoms. Lower alkyl by itself or as moiety of another substituent denotes $C_1$-$C_4$alkyl. Examples are methyl, ethyl, propyl, isopropyl, butyl, isobutyl, sec-butyl, tert-butyl, as well as the higher homologues amyl, isoamyl, hexyl, heptyl, octyl, together with their isomers. By analogy, alkanoyl or cyanoalkyl groups contain an additional carbon atom. Lower alkenyl or alkynyl groups accordingly contain not more than 4 carbon atoms.

The term "aliphatic group" comprises saturated radicals (alkyls), and unsaturated radicals (alkenyls, alkadienyls, alkynyls), halogen-substituted radicals, cyano-substituted radicals, and radicals which are interrupted by oxygen. These radicals contain not more than 8 carbon atoms.

The term "aromatic group" comprises phenyl and naphthyl, which can in principle be mono- or polysubstituted by CN, NO$_2$, halogen, lower alkyl, lower alkoxy or haloalkyl. An araliphatic radical comprises an unsubstituted or mono- to trisubstituted phenyl or naphthyl radical which is bonded through lower alkyl or lower alkenyl to the radical of the molecule. Examples are benzyl, phenethyl, phenylallyl and their homologues.

Unsubstituted or substituted heterocyclic radicals can be mono- or bicyclic. Examples are: furan, nitrofuran, bromofuran, methylfuran, thiophene, chlorothiophene, pyridine, 2,6-dichloropyridine, pyrimidine, pyridazine, pyrazine, piperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane or 1,4-oxathi-(2)-ine, benzthiazole, benzoxazole, benzimidazole, quinoline, benz-1,3-dioxolane. Cycloalkyl groups are cyclopropyl, cyclobutyl, cyclopentyl, cyclohexyl and cycloheptyl. Cycloaliphatic radicals correspond to these ring systems, but, where possible, can additionally contain one or more double bonds.

The compounds of the formula I can be obtained
(a) with the exception of compounds wherein $R_8$ is

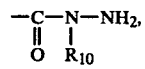

by reacting
a compound of the formula II

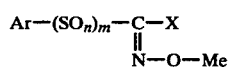      (II)

with a compound of the formula III

Hal'—Q      (III)

or
(b) where $R_8$ is

by reacting a compound of the formula IV

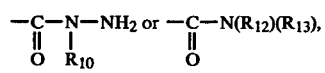      (IV)

with a compound of the formula V or VI

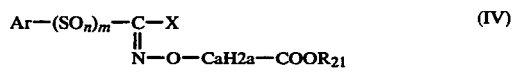      (V)

      (VI)

In the above formulae II, III, IV, V and VI, Ar, X, Q, m and n are as defined for formula I, Hal' is halogen, preferably chlorine or bromine, and Me is hydrogen or a metal cation, preferably the cation of an alkali metal or alkaline earth metal.

The compounds of the formula IV can be obtained by a process analogous to that of process (a).

The reactions can be carried out in the presence or absence of solvents which are inert to the reactants. Examples of suitable solvents are:
alcohols, such as ethanol; ketones, such as acetone; nitriles, such as acetonitrile; N,N-dialkylated amides, such as dimethyl formamide; dimethyl sulfoxide; pyridine; as well as mixtures of these solvents with one another.

Where Me is hydrogen, the process is carried out in the presence of a base. Examples of suitable bases are inorganic bases, such as the oxides, hydroxides, hydrides, carbonates and bicarbonates of alkali metals and alkaline earth metals, as well as e.g. tertiary amines, such as trialkylamines (e.g. triethylamine), and pyridine. The reaction temperatures are in the range between 0° and 150° C. The reactions are carried out under normal pressure and, in (a), optionally in a nitrogen atmosphere.

The compounds of the formula II are prepared by methods analogous to known ones. Processes (a) and (b) also constitute an object of the invention.

Compounds of the formula I can in principle also be obtained by other methods which are known per se (cf. Journ. für Prakt. Chemie 66, p. 353; Pharm. Zentr. Halle 55, p. 735; J. Med. Chem. 20, p. 1199).

Salts are likewise obtained by methods which are known per se.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active substance in commercial compositions is between 0.1% and 90% by weight.

For application, the compounds of the formula I may be processed to the following formulations (in which the percentages by weight in brackets refer to advantageous amounts of active ingredient):

Solid formulations;
  dusts, tracking agents, (up to 10%) granules (coated granules, impregnated granules and homogeneous granules); pellets (1 to 80%);

Liquid formulations:
  (a) active substances concentrates which are dispersible in water; wettable powders, pastes; (25–90% in commercial packs, 0.01 to 15% in ready for use solutions; emulsifiable concentrates and concentrated solutions (10 to 50%; 0.01 to 15% in ready for use solutions).
  (b) Solutions (0.1 to 20%), aerosols.

Such compositions also constitute an object of the invention.

Different compounds which are able to antagonise the harmful action of a herbicide on cultivated plants specifically have already been proposed as antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows or as tank mixture, by themselves or together with the herbicide or after emergence of the plants. The pre-emergence treatment includes both treatment of the crop area before sowing (ppi=pre-plant incorporation) and treatment of the crop areas after sowing but before emergence of the plants.

Thus, British patent specification No. 1 277 557 discloses the treatment of seed and seedlings of wheat and sorghum with certain esters and amides of oxamic acid before attack by N-methoxymethyl-2'-6'-diethylchloroacetanilide (Alachlor). Other publications (German Offenlegungsschriften 1 952 910 and 2 245 471, and French patent specification No. 2 021 611), propose antidotes for the treatment of cereals, maize seeds and rice seeds to protect them against attack by herbicidal thiolcarbamates. In German patent specification No. 1 576 676 and U.S. patent specification No. 3 131 509, hydroxyamino-acetanilides and hydantoins are suggested for protecting cereal seeds against carbamates, such as IPC, CIPC, etc.

The further development, however, has shown all these preparations to be unsatisfactory.

Surprisingly, oximes of the formula I have the property of protecting cultivated plants from attack by aggressive agrochemicals, in particular herbicides, of the most diverse compound classes, including 1,3,5-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyphenoxyacetates and -propionates, benzoic acid derivatives, where these compounds are not tolerated or insufficiently tolerated by plants.

The rates of application of the antidote with respect to the herbicide depend largely on the mode of application. Where a field treatment is carried out, the ratio of antidote of the formula I to phytotoxic chemical is 1:100 to 5:1, preferably 1:20 to 1:1. When dressing seeds and taking similar specific protective measures, however, much lower amounts of antidote are required in comparison with e.g. the amounts of herbicide later employed per hectare of crop area (e.g. about 1:3000 to 1:1000). As a rule, protective measures such as seed dressing with an antidote of the formula I and possible later field treatment with agrochemicals are only loosely connected. Pretreated seeds and plants can later come into contact with different chemicals in agriculture, horticulture and forestry.

Accordingly, the invention relates to plant protection compositions which contain, as active ingredient, solely an antidote of the formula I together with conventional carriers. If appropriate or desired, such compositions can additionally be mixed with the chemical against the action of which it is desired to protect the cultivated plant, for example with a herbicide.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals, maize, rice, millet, soybeans, beans, peas, potatoes, vegetables, cotton, sugar beet, sugar cane, ground nuts, tobacco, hops, and also ornamentals, fruit trees and bananas, cocoa and natural rubber plants. This list does not constitute a limitation.

In principle, an antidote can be employed wherever it is desired to protect a cultivated plant from the phytotoxicity of a chemical.

The invention also relates to a method of protecting cultivated plants from aggressive (phytotoxic) chemicals, which comprises applying an oxime derivative of the formula I which acts as antidote, optionally before or after application of the chemical, or also simultaneously with the chemical.

The invention also relates to the propagation products of such cultivated plants which are given a protective treatment with an oxime derivative of the formula I. By propagation products are meant all generative parts of plants which can be used for the propagation of the cultivated plant, for example grains (seeds in the narrow sense), roots, fruit, tubers, rhizomes, parts of stalks, branches (seedlings) and other parts of plants. Propagation products also include pregerminated plants and young plants which, after pregermination or emergence, will be further transplanted. Such young plants can be selectively protected by means of a complete or partial immersion treatment before transplantation.

The following types of substituents or combinations thereof with one another are preferred:
where Q is:

(a) CH$_2$CONHNH$_2$ (b) CH—CONHNH$_2$
    |
    CH$_3$ (c) C$_a$H$_{2a}$CONHNH$_2$ (d) 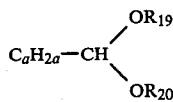

(e) C$_2$H$_{2a}$—CN(R$_{14}$)(R$_{15}$)
    ‖
    S (f) C$_a$H$_{2a}$—C—N(R$_{12}$)(R$_{13}$)
    ‖
    O where
a is: —1 or 2
Ar:

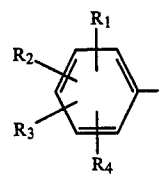

1-naphthyl

benzoxazole benzthiazole

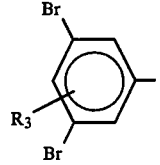

where
X is:
(a) cyano
(b) hydrogen
(c) a carboxylic acid ester radical
(d) lower alkyl
where
n and m are:
(a) n=2 m=1
(b) m=0

A group of compounds of the general formula

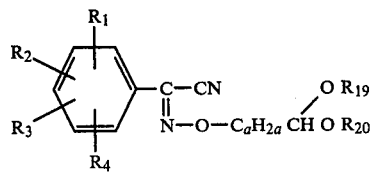

wherein a, R$_1$, R$_2$, R$_3$, R$_4$, R$_{19}$ and R$_{20}$ are as defined for formula I, possess in addition a plant growth-inhibiting action. They are particularly suitable for inhibiting the vegetative growth of soybean plants, without at the same time having a detrimental effect on the generative growth. This action results in smaller, stocky plants which are less susceptible to the influence of climate and weather and which produce a higher yield per crop area on the one hand because less energy need be expended on the vegetative growth, and, on the other hand, because it is possible to grow small plants closer together.

The invention is illustrated by the following Examples, but without any restriction to what is described therein. Temperatures are in degrees centigrade, pressures in millibars, and parts and percentages are by weight.

EXAMPLE 1

Manufacture of

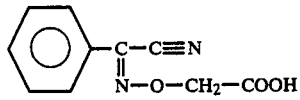

33.6 g of the sodium salt of α-phenylacetonitrile oxime is suspended in 200 ml of acetonitrile, then 23 g of the sodium salt of chloroacetic acid in 20 ml of water are added and the suspension is stirred for 1 hour under reflux. The reaction mixture is filtered hot and the filtrate is concentrated. The semi-solid residue is stirred in about 50 ml of cold water, filtered with suction and dried, affording 30.3 g of

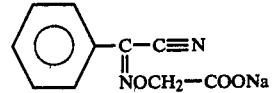

This product is dissolved hot in water, stirred with charcoal and filtered clear. The filtrate is acidified with 2N HCl and the white precipitate is collected by suction, washed and dried. Melting point: 169°–171° C.

EXAMPLE 2

Manufacture of

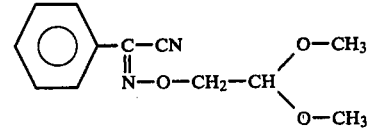

16.9 g (0.1 mole) of bromoacetaldehyde dimethyl acetate are added to a solution of 16.8 g (0.1 mole) of the sodium salt of α-phenacetonitrile oxime in 70 ml of dimethyl sulfoxide. The reaction mixture is heated for 4 hours to 60° C., diluted with 400 ml of ether and washed with three 200 ml portions of 2% NaOH. The ethereal solution is concentrated and the crude product is recrystallised from hexane. Yield: 14 g of crystals with a melting point of 35° C.

EXAMPLE 3

Manufacture of

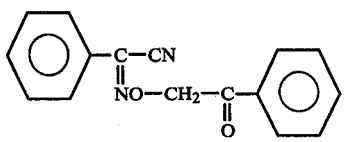

10 g of ω-bromoacetophenone are dissolved in 70 ml of acetonitrile and 8.5 g of the sodium salt of α-phenylacetonitrile oxime are added to the solution. The temperature is kept between 30° and 35° C. by cooling and the reaction mixture is stirred for 2 hours at room temperature and then concentrated to dryness. The residue is taken up in 200 ml of ether and ethereal solution is washed with two 200 ml portions of 3% NaOH solution, dried over MgSO₄ and concentrated. The crude product is recrystallised from ether/hexane, affording 6 g of light yellow crystals with a melting point of 80° C.

EXAMPLE 4

Manufacture of

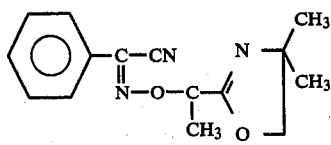

20.6 g (0.1 mole) of 2-[1-bromoethyl]-4,4-dimethyl oxazoline are added dropwise to a solution of 15.4 g (0.1 mole) of the sodium salt of α-phenylacetonitrile oxime in 70 ml of dimethyl sulfoxide. After the weakly exothermic reaction has subsided, the reaction mixture is diluted with 100 ml of ether and the dimethyl sulfoxide is washed out with three 300 ml portions of water. The ethereal phase is dried and concentrated. The resulting crystals are washed with hexane, affording 14.5 g of crystals with a melting point of 48° C.

EXAMPLE 5

Manufacture of

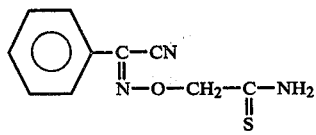

40 g (0.02 mole) of the compound

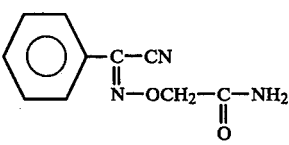

are dissolved in 20 ml of hexamethylphosphoric triamide and to the solution are then added 4.0 g (0.01 mole) of dimeric p-methoxyphenylthionophosphine sulfide. The resultant suspension is heated for 30 minutes to 80° C. After cooling, the reaction mixture is poured into 50 ml of water and the precipitated oil is extracted with ether. The extract is dried and concentrated and the residue is filtered with ether over a small column of silica gel. Evaporation of the filtrate affords 3.4 g of light brown crystals with a melting point of m.p. 104°–106° C.

EXAMPLE 6

Manufacture of

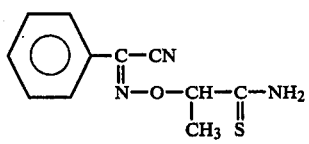

7.6 g (0.05 mole) of 2-bromopropionamide is dissolved in 30 ml of hexametapol and then 10.1 g (0.025 mole) of dimeric p-methoxyphenylthionophosphine sulfide are added at room temperature. The reaction is slightly exothermic and the temperature rises to 33° C. The reaction mixture is stirred for 30 minutes at 80° C. and then cooled to 40° C. To the clear yellow solution are added 9.9 g (0.05 mole) of the sodium salt of α-phenylacetonitrile oxime (85%) which additionally contains about 15% of isopropanol. The reaction is exothermic and the temperature rises to 52° C. The resultant yellow suspension is stirred for 10 minutes at 45° C. The reaction mixture is then poured into 100 ml of water and extracted with methylene chloride. The organic phase is dried and concentrated by rotary evaporation and the residue is chromatographed over a silica gel column with petroleum ether/ether (5:1). The main fraction is concentrated, affording 7.3 g (62.9%) of yellow crystals with a melting point of 85°–90° C.

The following compounds of the formula (I) can be obtained in analogous manner or by one of the methods described herein.

TABLE I

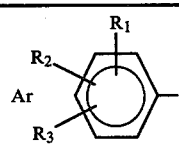

| Compound | $R_1$ | $R_2$ | $R_3$ | m | n | X | Q | Physical data (°C.) |
|---|---|---|---|---|---|---|---|---|
| 1 | H | H | H | 0 | — | CN | —CH₂COONa | |
| 2 | H | H | H | 0 | — | CN | —CH₂COOH | m.p. 169–171° |
| 3 | H | H | H | 0 | — | CN | —CH₂—CH(OCH₃)₂ | m.p. 35° |
| 4 | H | H | H | 0 | — | CN | —CH₂COC₆H₅ | m.p. 80° |

TABLE I-continued $$\text{Ar} - \begin{array}{c} R_1 \\ R_2 \\ R_3 \end{array}$$

| Compound | R₁ | R₂ | R₃ | m | n | X | Q | Physical data (°C.) |
|---|---|---|---|---|---|---|---|---|
| 5 | H | H | H | 0 | — | CN | −CH(CH₃)−C(CH₃)₂−N=... (oxazoline) | m.p. 48° |
| 6 | H | H | H | 0 | — | CN | −CH₂CSNH₂ | m.p. 104–106° |
| 7 | H | H | H | 0 | — | CN | −CH(CH₃)CSNH₂ | m.p. 85–90° |
| 8 | H | H | H | 0 | — | CN | −CH₂−CO−N(CH₃)(CHO) | m.p. 83° |
| 9 | H | H | H | 0 | — | CN | −CH₂−CO−N(morpholino) | m.p. 114–116° |
| 10 | H | H | H | 0 | — | CN | −CH₂CONHCOOCH₃ | m.p. 137–138° |
| 11 | H | H | H | 0 | — | CN | −CH₂CONHCONH₂ | m.p. 182–183° |
| 12 | H | H | H | 0 | — | CN | −CH₂CONHCOOC₂H₅ | |
| 13 | 2-Cl | 4-Cl | H | 0 | — | CN | −CH₂CONHCONH₂ | m.p. 179–182° |
| 14 | 2-Cl | 4-Cl | H | 0 | — | CN | −CH₂CONHCOOCH₃ | |
| 15 | 2-Cl | 4-Cl | H | 0 | — | CN | −CH₂CON(CH₃)(CHO) | viscous oil |
| 16 | H | H | H | 1 | 2 | CN | −CH₂CON(CH₃)(CHO) | m.p. 127–130° |
| 17 | H | H | H | 1 | 2 | CN | −CH₂CONHCONH₂ | m.p. 160–163° |
| 18 | H | 4-CH₃ | H | 1 | 2 | CN | −CH₂CONHCOOCH₃ | m.p. 167–168° |
| 19 | H | H | H | 0 | — | CN | −CH₂CONHNH₂ | m.p. 129–131° |
| 20 | H | H | H | 0 | — | CN | −CH(CH₃)CONHNH₂ | m.p. 116–119° |
| 21 | H | 4-Cl | H | 0 | — | CN | −CH₂CONHNH₂ | m.p. 139–141° |
| 22 | H | 4-Cl | H | 0 | — | CN | −CH(CH₃)CONHNH₂ | m.p. 162–163° |
| 23 | 4-CH₃ | H | H | 0 | — | CN | −CH(CH₃)CONHNH₂ | |
| 24 | 2-Cl | 4-Cl | H | 0 | — | CN | −CH₂CONHNH₂ | |
| 25 | 2-Cl | 4-Cl | H | 0 | — | CN | −CH(CH₃)CONHNH₂ | |
| 26 | H | H | H | 0 | — | CN | −CH₂COON(C₄H₉)₄ | |
| 27 | H | H | H | 0 | — | CN | −CH₂CO−ON(CH₂CH₂OH)₂ | |
| 28 | H | 3-Cl | H | 0 | — | CH₃ | −CH₂COOH | m.p. 93–95° |
| 29 | H | 4-Cl | H | 0 | — | CH₃ | −CH₂COOH | m.p. 117–120° |
| 30 | H | 4-CH₃ | H | 0 | — | CH₃ | −CH₂COOH | m.p. 114–116° |
| 31 | 3-CH₃ | 4-Cl | H | 0 | — | CH₃ | −CH₂COOH | m.p. 97–101° |
| 32 | 2-Cl | 4-Cl | H | 0 | — | CH₃ | −CH₂COOH | m.p. 86–88° |
| 33 | H | 4-Cl | H | 0 | — | CN | −CH₂CH₂COOH | |
| 34 | H | 4-Cl | H | 0 | — | CH₃ | −CH₂CH₂COOH | m.p. 80–83° |

TABLE I-continued structure: Ar-benzene ring with R1, R2, R3 substituents

| Compound | R1 | R2 | R3 | m | n | X | Q | Physical data (°C.) |
|---|---|---|---|---|---|---|---|---|
| 35 | H | 4-Cl | H | 0 | — | CH₃ | —CH₂CH₂CH₂—COOH | m.p. 106–8° |
| 36 | H | 4-Cl | H | 0 | — | CH₃ | —CH(CH₃)—COOH | m.p. 87–89° |
| 37 | H | H | H | 0 | — | CN | —CH₂CO—N(2-methylpiperidine) | oil |
| 38 | H | 4-CH₃ | H | 1 | 2 | CN | —CH₂CO—N(morpholine) | m.p. 142–145° |
| 39 | H | H | H | 0 | — | CN | —CH₂COCH₃ | m.p. 68° |
| 40 | H | H | H | 0 | — | CN | —CH₂—(1,3-dioxolane) | m.p. 67° |
| 41 | H | H | H | 0 | — | CN | —CH₂—(1,3-dioxane) | m.p. 52–53° |
| 42 | H | H | H | 0 | — | CN | —CH₂—(5,5-dimethyl-1,3-dioxane) | m.p. ~30° |
| 43 | H | H | H | 0 | — | CN | —CH₂—(2,4,4-trimethyl-1,3-dioxane) | m.p. 60° |
| 44 | H | H | H | 0 | — | CN | —CH₂CH(OC₂H₅)₂ | $n_D^{21}$ = 1.5110 |
| 45 | H | 4-CH₃ | H | 0 | — | CN | —CH₂—(2,4,4-trimethyl-1,3-dioxane) | m.p. 97° |
| 46 | H | 2-Cl | H | 0 | — | CN | —CH₂—(2,4,4-trimethyl-1,3-dioxane) | $n_D^{24}$ = 1.5170 |

TABLE I-continued $$\text{Ar} - \underset{\underset{R_3}{\overset{R_2}{\bigcirc}}}{\overset{R_1}{}}$$

| Compound | R₁ | R₂ | R₃ | m | n | X | Q | Physical data (°C.) |
|---|---|---|---|---|---|---|---|---|
| 47 | H | 4-Cl | H | O | — | CH₃ | —CH(CH₃)—COOH | m.p. 84–85° |
| 48 | H | 4-CH₃O | H | 0 | — | CN | —CH₂—CH(O—C(CH₃)₂—CH₂—CH(CH₃)—O) (1,3-dioxane ring) | $n_D^{24} = 1.5281$ |
| 49 | H | 2-Cl | H | 0 | — | CN | —CH₂—CH(OCH₃)₂ | $n_D^{24}$ 1.5304 |
| 50 | H | 4-CH₃ | H | 0 | — | CN | —CH₂—CH(OCH₃)₂ | $n_D^{24} = 1.5258$ |
| 51 | H | 4-CH₃O | H | 0 | — | CN | —CH₂—CH(OCH₃)₂ | $n_D^{24} = 1.5375$ |
| 52 | 3-Cl | 4-Cl | H | 0 | — | CN | —CH₂—CH(O—C(CH₃)₂—CH₂—CH(CH₃)—O) | $n_D^{24} = 1.5354$ |
| 53 | 3-Cl | 4-Cl | H | 0 | — | CN | —CH₂—CH(OCH₃)₂ | $n_D^{22} = 1.5523$ |
| 54 | 3-Cl | 4-Cl | H | 0 | — | CN | —CH₂—CH(O—C(CH₃)₂—C(CH₃)₂—O) | $n_D^{22} = 1.5355$ |
| 55 | H | 2-Cl | H | 0 | — | CN | —CH₂—CH(O—C(CH₃)₂—C(CH₃)₂—O) | $n_D^{22} = 1.5236$ |
| 56 | H | 4-CH₃O | H | 0 | — | CN | —CH₂—CH(O—C(CH₃)₂—C(CH₃)₂—O) | m.p. 85° |
| 57 | H | 4-CH₃ | H | 0 | — | CN | —CH₂—CH(O—C(CH₃)₂—C(CH₃)₂—O) | m.p. 75° |
| 58 | H | 4-CH₃O | H | 0 | — | CN | —CH₂CH₂—CH(O—CH₂—CH₂—O) (1,3-dioxolane) | $n_D^{21} = 1.5437$ |
| 59 | H | 2-Cl | H | 0 | — | CN | —CH₂CH₂—CH(O—CH₂—CH₂—O) | $n_D^{24.5} = 1.5435$ |
| 60 | 3-Cl | 4-Cl | H | 0 | — | CN | —CH₂CH₂—CH(O—CH₂—CH₂—O) | wax |

TABLE I-continued $$\text{Ar} \underset{R_3}{\overset{R_2}{\underset{}{\bigcirc}}} \overset{R_1}{}$$

| Compound | R₁ | R₂ | R₃ | m | n | X | Q | Physical data (°C.) |
|---|---|---|---|---|---|---|---|---|
| 61 | H | H | H | O | — | CN | —CH₂CH₂—CH(O—CH₂—CH₂—O) (dioxolane) | $n_D^{24} = 1.5443$ |
| 62 | H | 4-CN | H | O | — | COOCH₃ | CH₂CONHNH₂ | |
| 63 | H | 4-CN | H | O | — | CH₃ | CH₂COOH | |
| 64 | H | 4-CN | H | O | — | CN | CH₂CH₂CONHNH₂ | |
| 65 | H | 4-CN | H | O | — | CN | CH₂CH(O—CH₂—O) (dioxolane) | |
| 66 | H | 2-CN | H | O | — | CN | CH₂CONHCOC₆H₅ | |
| 67 | H | 4-NO₂ | H | O | — | CH₃ | CH₂CONHNH₂ | |
| 68 | H | 4-NO₂ | H | O | — | CN | CH₂CH₂CON(piperidine) | |
| 69 | H | 2-CH₃ | 4-OCO—NH—CH₃ | O | — | CH₃ | CH(CH₃)—CONC₆H₅ · NH₂O | |
| 70 | 3-OCH₃ | 2-NO₂ | 4-OCO—CH₃ | O | — | CN | CH(CH₃)COO⁻⊕NH₄ | |
| 71 | 3-Cl | 2-OCOCH₃ | 5-Cl | O | — | CH₃ | CH₂—CH(O—CH₂—CH₂—O) (dioxane) | |
| 72 | 4-CH₃ | 2-OCOCH₃ | 6-CH₃ | O | — | H | CH(CH₃)COO⁻⊕Na | |
| 73 | H | 4-N(C₂H₅)₂ | H | O | — | CH₃ | CH₂—CH(O—CH₂—C(CH₃)₂—O) | |
| 74 | 3-CH₃ | 5-CH₃ | H | O | — | CH₃ | CH₂—COCH₃ | |
| 75 | H | 4-Cyclohexyl | H | O | — | H | CH₂—CO—C₆H₅ | |
| 76 | H | 4-Br | H | O | — | CONHCH₃ | CH₂CONHNH₂ | |
| 77 | H | 2-OCH₂—C₆H₅ | H | O | — | CH₃ | CH₂CON(CH₃)COCH₂Cl | |
| 78 | H | 4-C₆H₄Br(4) | H | O | — | CH₃ | CH₂CON(morpholine) | |
| 79 | H | 4-OCH₂C₆H₅ | H | O | — | CH₃ | CH₂CON(2,2,6,6-tetramethylpiperidine) | |
| 80 | H | 4-CH=CH—C₆H₅ | H | O | — | CH₃ | CH₂COCH₃ | |

TABLE I-continued $$\text{Ar} \underset{R_3}{\overset{R_2}{\bigcirc}} R_1$$

| Compound | R₁ | R₂ | R₃ | m | n | X | Q | Physical data (°C.) |
|---|---|---|---|---|---|---|---|---|
| 81 | 3-Cl | 2-OCOCH₃ | 6-Cl | O | — | C₂H₅ | CH₂—CH(OCH₃)₂ | |
| 82 | 3-Cl | 2-OCOCH₃ | 6-Cl | O | — | CH₃ | CH₂—CH(OC₂H₅)₂ | |
| 83 | 5-Cl | 2-OCONHCH₃ | H | O | — | CH₃ | CH₂CH₂CH₂CONHNH₂ | |
| 84 | 2-Cl | H | H | O | — | CN | $-CH_2-\overset{O}{\underset{O}{\diagup\diagdown}}$ | m.p. 39° |
| 85 | H | H | H | O | — | CN | CH₂CO—⟨⟩—OCH₃ | m.p. 96–8° |
| 86 | H | 4-OCH₃ | H | O | — | CN | CH₂CH(OC₂H₅)₂ | $n_D^{22} = 1.5250$ |
| 87 | 2-Cl | 4-Cl | H | O | — | CN | CH₂CH(OC₂H₅) | $n_D^{22} = 1.5237$ |
| 88 | H | H | H | O | — | CN | C₂H₄CH(OC₂H₅)₂ | $n_D^{20} = 1.4947$ |
| 89 | | 2,3-C₄H₄— | H | O | — | CN | CH₂CH(OC₂H₅)₂ | $n_D^{20} = 1.5462$ |
| 90 | 4-CH₃ | H | H | O | — | CN | $-CH_2-CH\overset{O}{\underset{O}{\diagup\diagdown}}$ | m.p. 55° |
| 91 | 4-OCH₃ | H | H | O | — | CN | $-CH_2-CH\overset{O}{\underset{O}{\diagup\diagdown}}$ | m.p. 55° |
| 92 | 4-Cl | 3-Cl | H | O | — | CN | $-CH_2-CH\overset{O}{\underset{O}{\diagup\diagdown}}$ | m.p. 65° |
| 93 | 4-CH₃ | H | H | O | — | CN | $-CH_2-CH\overset{O}{\underset{O}{\diagup\diagdown}}$ | m.p. 59° |
| 94 | 4-OCH₃ | H | H | O | — | CN | $-CH_2-CH\overset{O}{\underset{O}{\diagup\diagdown}}$ | m.p. 59° |
| 95 | 2-Cl | H | H | O | — | CN | $-CH_2-CH\overset{O}{\underset{O}{\diagup\diagdown}}$ | |
| 96 | 4-Cl | 3-Cl | H | O | — | CN | $-CH_2-CH\overset{O}{\underset{O}{\diagup\diagdown}}$ | |
| 97 | 4-OCH₃ | H | H | O | — | CN | $-CH_2-CH_2-CH\overset{O}{\underset{O}{\diagup\diagdown}}$ | $n_D^{24} = 1.5492$ |

TABLE I-continued

| Compound | $R_1$ | $R_2$ | $R_3$ | m | n | X | Q | Physicial data (°C.) |
|---|---|---|---|---|---|---|---|---|
| 98 | H | H | H | O | — | CN | −CH$_2$−CH$_2$−CH(−O−CH$_2$−CH$_2$−O−) (1,3-dioxolane) | $n_D^{23.5} = 1.5420$ |
| 99 | H | H | H | O | — | CN | −CH(CH$_3$)−C(=O)−C$_6$H$_5$ | m.p. 85° |
| 100 | H | H | H | O | — | CN | −CH$_2$−C(=O)−C$_6$H$_4$−Cl | m.p. 97° |
| 101 | H | H | H | O | — | CN | −CH$_2$−C(=O)−C$_6$H$_4$−Br | m.p. 111° |
| 102 | 4-CH$_3$ | H | H | O | — | CN | −CH$_2$−CH(OC$_2$H$_5$)$_2$ | $n_D^{21.5} = 1.5149$ |
| 103 | 4-Cl | 3-Cl | H | O | — | CN | −CH$_2$−CH(OC$_2$H$_5$)$_2$ | $n_D^{22} = 1.5303$ |
| 104 | 4-Cl | H | H | O | — | CN | −CH$_2$−CH(OC$_2$H$_5$)$_2$ | $n_D^{20} = 1.5190$ |
| 105 | 4-CH$_3$ | H | H | O | — | CN | −CH$_2$−CH$_2$−CH(OC$_2$H$_5$)$_2$ | $n_D^{24} = 1.5008$ |
| 106 | 4-OCH$_3$ | H | H | O | — | CN | −CH$_2$−CH$_2$−CH(OC$_2$H$_5$)$_2$ | $n_D^{24} = 1.5114$ |
| 107 | 4-Cl | 3-Cl | H | O | — | CN | −CH$_2$−CH$_2$−CH(OC$_2$H$_5$)$_2$ | $n_D^{24} = 1.5220$ |
| 108 | 4-Cl | 2-Cl | H | O | — | CN | −CH$_2$−CH$_2$−CH(OC$_2$H$_5$)$_2$ | $n_D^{24} = 1.5143$ |
| 109 | 4-Cl | H | H | O | — | CN | −CH$_2$−CH$_2$−CH(OC$_2$H$_5$)$_2$ | $n_D^{24} = 1.5103$ |
| 110 |  | 2,3-C$_4$H$_4$− | H | O | — | CN | −CH$_2$−CH$_2$−CH(OC$_2$H$_5$)$_2$ | $n_D^{24} = 1.5400$ |
| 111 | 4-Cl | 2-Cl | H | O | — | CN | −CH$_2$−CH(−O−CH$_2$−O−) (1,3-dioxolane) | $n_D^{24} = 1.5474$ |
| 112 | 4-Cl | H | H | O | — | CN | −CH$_2$−CH(−O−CH$_2$−O−) (1,3-dioxolane) | $n_D^{24} = 1.5493$ |
| 113 |  | 2,3-C$_4$H$_4$− | H | O | — | CN | −CH$_2$−CH(−O−CH$_2$−O−) (1,3-dioxolane) | $n_D^{24} = 1.5842$ |
| 114 | 4-Cl | 2-Cl | H | O | — | CN | −CH$_2$−CH(OCH$_3$)$_2$ | $n_D^{24} = 1.5428$ |
| 115 |  | 2,3-C$_4$H$_4$− | H | O | — | CN | −CH$_2$−CH(OCH$_3$)$_2$ | $n_D^{24} = 1.5707$ |
| 116 | 4-Cl | 2-Cl | H | O | — | CN | −CH$_2$−CH(−O−C(CH$_3$)$_2$−CH$_2$−O−) | $n_D^{24} = 1.5377$ |

TABLE I-continued

![Structure: Ar-substituted benzene ring with R1, R2, R3 substituents]

| Compound | R₁ | R₂ | R₃ | m | n | X | Q | Physical data (°C.) |
|---|---|---|---|---|---|---|---|---|
| 117 | 4-CH₃ | H | H | O | — | CN | —CH(CH₃)—C(O)—C₆H₅ | $n_D^{22} = 1.5826$ |
| 118 | 4-OCH₃ | H | H | O | — | CN | —CH(CH₃)—C(O)—C₆H₅ | m.p. 64–65° |
| 119 | 4-Cl | 3-Cl | H | O | — | CN | —CH(CH₃)—C(O)—C₆H₅ | $n_D^{22} = 1.5995$ |
| 120 | H | H | H | O | — | CN | —CH₂—CH(O—)(O—)C(Et)₂ (dioxane w/ 2 Et) | $n_D^{22} = 1.5266$ |
| 121 | 4-CH₃ | H | H | O | — | CN | —CH₂—CH(O—)(O—)C(Et)₂ | m.p. 118–120° |
| 122 | 4-Cl | 3-Cl | H | O | — | CN | —CH₂—CH(O—)(O—)C(Et)₂ | m.p. 88–95° |
| 123 | 3-CF₃ | H | H | O | — | CN | —CH₂CON(CH₃)CHO | |
| 124 | 3-CF₃ | H | H | O | — | CN | —CH₂CONHNH₂ | |
| 125 | 3-CF₃ | H | H | O | — | CN | —CH₂CONHCOOCH₃ | |
| 126 | 3-CF₃ | H | H | O | — | CN | —CH₂CONHCONH₂ | |
| 127 | 3-CF₃ | H | H | O | — | CN | —CH₂—CON(piperidyl-2-CH₃) | |
| 128 | 3-CF₃ | H | H | O | — | CN | —CH₂CH(OCH₃)₂ | |
| 129 | 3-CF₃ | H | H | O | — | CN | —CH₂CH(OC₂H₅)₂ | |
| 130 | 3-CF₃ | H | H | O | — | CN | —CH₂CH(O—)(O—) (1,3-dioxolane) | |
| 131 | 3-CF₃ | H | H | O | — | CN | —CH₂CH(O—)(O—) (1,3-dioxane) | |
| 132 | 3-CF₃ | H | H | O | — | CN | —CH₂CH(O—)(O—)C(CH₃)₂ (1,3-dioxane w/ gem-dimethyl) | |
| 133 | 3-Cl | H | H | O | — | CN | —CH₂CH(OCH₃)₂ | |
| 134 | 3-Cl | H | H | O | — | CN | —CH₂CH(OC₂H₅)₂ | |

TABLE I-continued

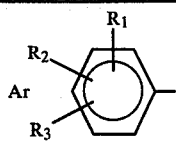

| Compound | R₁ | R₂ | R₃ | m | n | X | Q | Physical data (°C.) |
|---|---|---|---|---|---|---|---|---|
| 135 | 3-Cl | H | H | O | — | CN | —CH₂CH(O-)(O-)(CH₃)₂ (1,3-dioxane with gem-dimethyl) | |
| 136 | 3-CH₃ | H | H | O | — | | —CH₂CH(O-)(O-) (1,3-dioxolane) | |
| 137 | 3-OCH₃ | H | H | O | — | CN | —CH₂CH(OCH₃)₃ | |
| 138 | 3-CH₃ | H | H | O | — | CN | —CH(OCH₂)— | |
| 139 | 3-CH₃ | H | H | O | — | CN | —CH(OC₂H₅)₂ | |
| 140 | 3-OCH₃ | H | H | O | — | CN | —CH₂CH(O-)(O-) (1,3-dioxolane) | |

TABLE II (Ar = 3,4-dibromophenyl; X = H, m = O)

| Compound | R₃ | Q |
|---|---|---|
| 141 | 4-OCONHCH₃ | CH₂CONHNH₂ |
| 142 | 4-OCONHCH₃ | CH₂—CH(OCH₃)₂ |
| 143 | 4-OCONHCH₃ | CH₂—CH(OC₂H₅)₂ |
| 144 | 4-OCONHCH₃ | CH₂—CH(O-)(O-) (1,3-dioxolane) |
| 145 | 4-OCONHCH₃ | CH₂—CH₂—CH(O-)(O-) (1,3-dioxane) |
| 146 | 4-OCOCH₃ | CH₂CONHNH₂ |
| 147 | 4-OCOCH₃ | CH₂—CH(OCH₃)₂ |
| 148 | 4-OCOCH₃ | CH₂—CH(O-)(O-) (1,3-dioxolane) |
| 149 | 4-OCONHC₂H₅ | CH₂—CH(O-)(O-) (1,3-dioxane) |

TABLE II-continued (Ar = 3,4-dibromophenyl; X = H, m = O)

| Compound | R₃ | Q |
|---|---|---|
| 150 | 4-OCONHC₆H₅ | CH₂—(O-)(O-) (1,3-dioxolane) |
| 151 | 4-OCONHC₆H₅ | CH₂—(O-)(O-)C(CH₃)₂ (5,5-dimethyl-1,3-dioxane) |
| 152 | 4-OCONHC₂H₅ | CH₂CH(OC₂H₅)₂ |
| 153 | 2-OCH₂CH=CH₂ | CH₂CONHNH₂ |
| 154 | 2-OCH₂CH=CH₂ | CH₂CH₂—(O-)(O-) (1,3-dioxolane) |
| 155 | 2-OCH₂CH=CH₂ | CH₂—(O-)(O-) (1,3-dioxolane) |
| 156 | 4-OCH₂CH=CH₂ | CH₂—(O-)(O-)C(CH₃)₂ (5,5-dimethyl-1,3-dioxane) |

TABLE II-continued

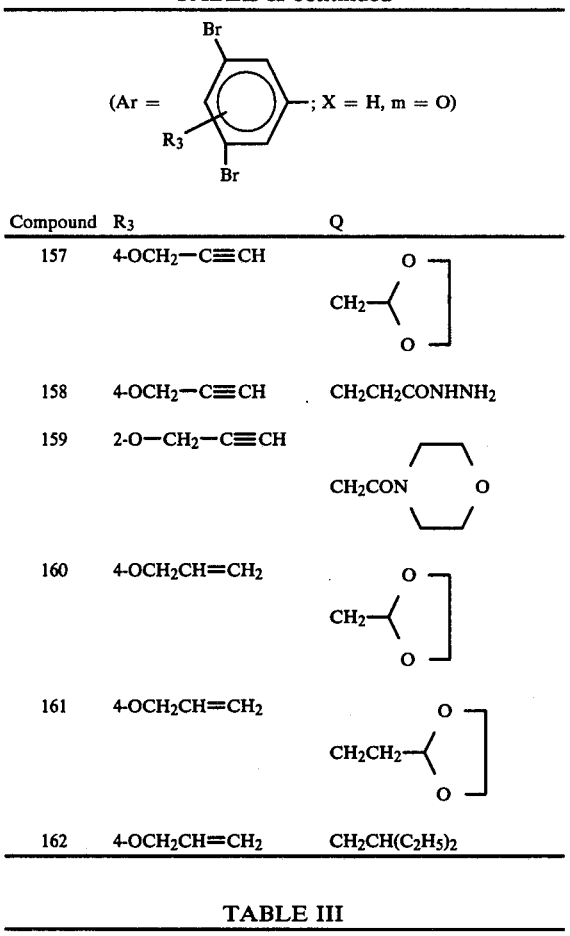

(Ar = [3,4-dibromophenyl with R3]; X = H, m = 0)

| Compound | R3 | Q |
|---|---|---|
| 157 | 4-OCH2—C≡CH | CH2-CH(O-CH2-O) (1,3-dioxolane) |
| 158 | 4-OCH2—C≡CH | CH2CH2CONHNH2 |
| 159 | 2-O—CH2—C≡CH | CH2CON(morpholino) |
| 160 | 4-OCH2CH=CH2 | CH2-CH(O-CH2-O) (1,3-dioxolane) |
| 161 | 4-OCH2CH=CH2 | CH2CH2-CH(O-CH2-O) (1,3-dioxane) |
| 162 | 4-OCH2CH=CH2 | CH2CH(C2H5)2 |

TABLE III

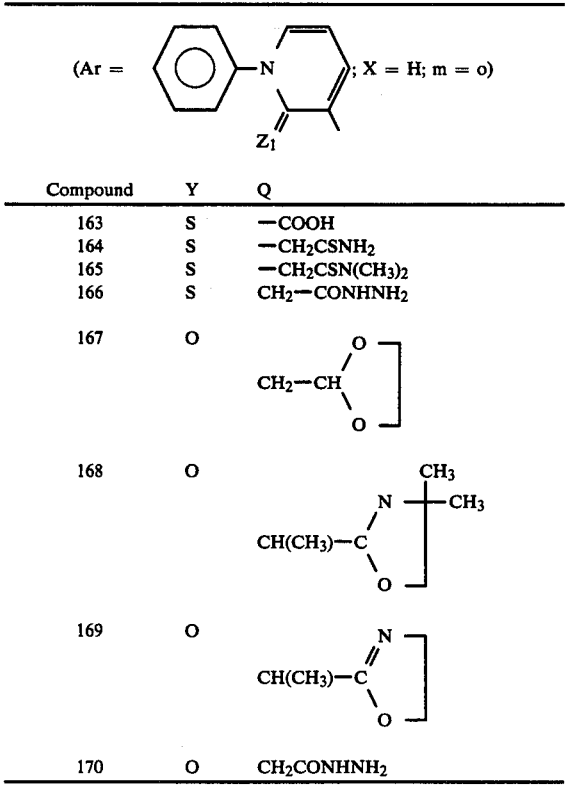

(Ar = phenyl-N-pyridyl with Z1; X = H; m = o)

| Compound | Y | Q |
|---|---|---|
| 163 | S | —COOH |
| 164 | S | —CH2CSNH2 |
| 165 | S | —CH2CSN(CH3)2 |
| 166 | S | CH2—CONHNH2 |
| 167 | O | CH2—CH(O-CH2-O) |
| 168 | O | CH(CH3)—C(oxazoline with gem-dimethyl) |
| 169 | O | CH(CH3)—C(oxazoline) |
| 170 | O | CH2CONHNH2 |

TABLE IV

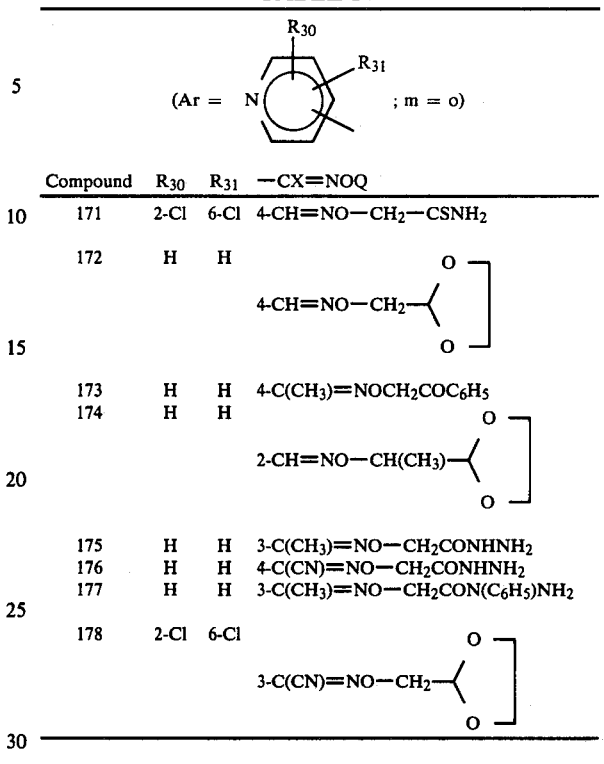

(Ar = pyridyl with R30, R31; m = o)

| Compound | R30 | R31 | —CX=NOQ |
|---|---|---|---|
| 171 | 2-Cl | 6-Cl | 4-CH=NO—CH2—CSNH2 |
| 172 | H | H | 4-CH=NO—CH2-C(O-CH2-O) |
| 173 | H | H | 4-C(CH3)=NOCH2COC6H5 |
| 174 | H | H | 2-CH=NO—CH(CH3)-C(O-CH2-O) |
| 175 | H | H | 3-C(CH3)=NO—CH2CONHNH2 |
| 176 | H | H | 4-C(CN)=NO—CH2CONHNH2 |
| 177 | H | H | 3-C(CH3)=NO—CH2CON(C6H5)NH2 |
| 178 | 2-Cl | 6-Cl | 3-C(CN)=NO—CH2-C(O-CH2-O) |

TABLE V

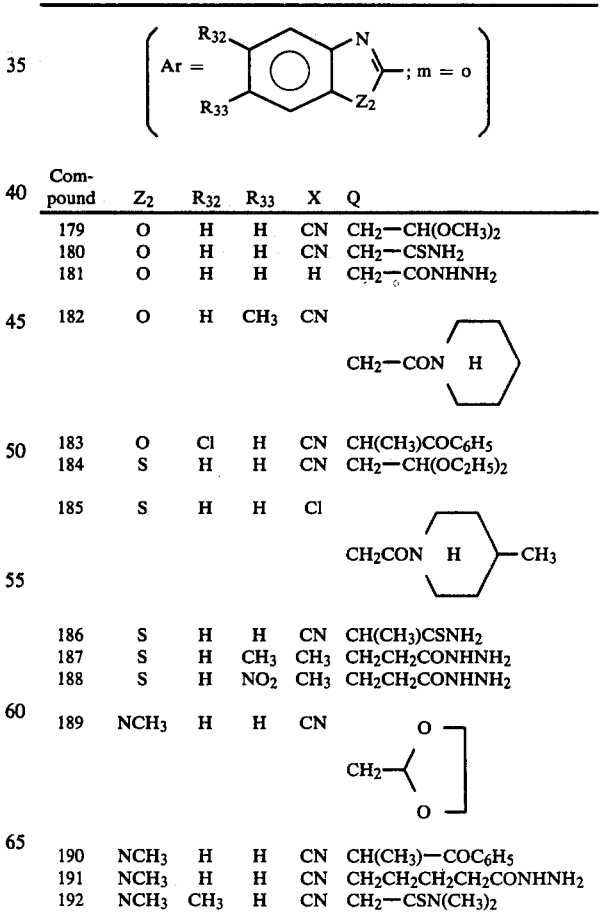

(Ar = benzoxazole/benzothiazole with R32, R33, Z2; m = o)

| Compound | Z2 | R32 | R33 | X | Q |
|---|---|---|---|---|---|
| 179 | O | H | H | CN | CH2—CH(OCH3)2 |
| 180 | O | H | H | CN | CH2—CSNH2 |
| 181 | O | H | H | H | CH2—CONHNH2 |
| 182 | O | H | CH3 | CN | CH2—CON(piperidino) |
| 183 | O | Cl | H | CN | CH(CH3)COC6H5 |
| 184 | S | H | H | CN | CH2—CH(OC2H5)2 |
| 185 | S | H | H | Cl | CH2CON(4-methylpiperidino) |
| 186 | S | H | H | CN | CH(CH3)CSNH2 |
| 187 | S | H | CH3 | CH3 | CH2CH2CONHNH2 |
| 188 | S | H | NO2 | CH3 | CH2CH2CONHNH2 |
| 189 | NCH3 | H | H | CN | CH2-C(O-CH2-O) |
| 190 | NCH3 | H | H | CN | CH(CH3)—COC6H5 |
| 191 | NCH3 | H | H | CN | CH2CH2CH2CH2CONHNH2 |
| 192 | NCH3 | CH3 | H | CN | CH2—CSN(CH3)2 |

TABLE V-continued $$\left(Ar = \begin{array}{c} R_{32} \\ R_{33} \end{array} \begin{array}{c} N \\ Z_2 \end{array}; m = o\right)$$

| Compound | $Z_2$ | $R_{32}$ | $R_{33}$ | X | Q |
|---|---|---|---|---|---|
| 193 | $NCH_3$ | Cl | H | $CH_3$ | $CH_2-CONCOC_6H_4Cl(4)$<br>        $\|$<br>       $C_2H_5$ |

TABLE VI $$\left(Ar = \text{phenyl-N=N-N=}\overset{R_{34}}{}; m = o; X = H\right)$$

| Compound | $R_{34}$ | Q |
|---|---|---|
| 194 | H | $CH_2CH(OCH_3)_2$ |
| 195 | $CH_3$ | $CH_2CH_2CONHNH_2$ |
| 196 | H | $(CH_2)_4CSN(CH_3)C_3H_7(n)$ |

TABLE VII $$\left(Ar = \begin{array}{c} R_{35} \\ R_{36} \end{array} \text{with } Z_3, \text{Cl}; m = o; X = O\right)$$

| Compound | $Z_3$ | $R_{35}$ | $R_{36}$ | Q |
|---|---|---|---|---|
| 197 | O | H | Cl | $CH(CH_3)-$ dioxolane |
| 198 | O | H | Cl | $CH_2CON(C_6H_5)NH_2$ |
| 199 | O | Cl | H | $CH(C_2H_5)CON(CH_3)COC_3H_7(n)$ |
| 200 | O | Cl | Cl | $CH_2CH_2CSNHC_6H_5$ |
| 201 | O | H | H | $CH_2CH_2CSNHC_6H_3(CH_3)_2(2.4)$ |
| 202 | S | H | Cl | $CH(C_2H_5)CON(C_3H_7)(n)$<br>                    $\|$<br>                   $COC_3H_7n$ |
| 203 | S | Cl | Cl | $CH_2COOH$ |
| 204 | S | Cl | Cl | $CH_2COO^\ominus \oplus Na$ |

TABLE VIII $$\left(Ar = \begin{array}{c} R_{37} \\ Z_4 \end{array}; m = o\right)$$

| Compound | $Z_4$ | $R_{37}$ | X | Q |
|---|---|---|---|---|
| 205 | S | H | CN | $CH(CH_3)-CSNHC_6H_3(CH_3)_2(2.6)$ |
| 206 | S | H | Cl | $CH_2CON\text{(piperidinyl)}$ |
| 207 | S | H | CN | $CH_2CH_2CONHNH_2$ |
| 208 | S | H | CN | $CH_2CSNH_2$ |
| 209 | S | Cl | CN | $CH_2CONC_4H_9n$<br>        $\|$<br>       $COC_6H_5$ |
| 210 | S | Cl | $CH_3$ | $CH(C_3H_7)CONHNH_2$ |
| 211 | O | Cl | CN | $CH_2CH_2CH_2CONHNH_2$ |
| 212 | O | Cl | $CH_3$ | $CH_2CH_2CH_2CSNH-C_6H_4Cl(2)$ |
| 213 | O | Cl | Cl | $CH_2-CON\text{(4-methylpiperidinyl)}$ |
| 214 | O | H | CN | $CH_2-CH\text{(5,5-dimethyl-1,3-dioxane)}$ |
| 215 | O | H | CN | $CH_2-CSNH_2$ |
| 216 | O | H | $CH_3$ | $CH_2-CON\text{(morpholino/oxazinyl)}$ |
| 217 | O | H | $CH_3$ | $C(-CH_3)_2CONHNH_2$ |
| 218 | O | H | Cl | $CH_2-CON\text{(4-methylpiperidinyl)}$ |
| 219 | O | H | CN | $C(CH_3)-COCH_3$ |
| 220 | $NCH_3$ | H | CN | $CH_2CONHNH_2$ |
| 221 | $NCH_3$ | H | CN | $CH_2CH_2CONHNH_2$ |
| 222 | $NCH_3$ | H | $CH_3$ | $CH(CH_3)CON\text{(piperidinyl)}$ |
| 223 | S | Cl | $CH_3$ | $CH_2COOH$ |

TABLE IX $$\left(Ar = \text{quinolinyl with } R_{38}; m = o; X = CH_3\right)$$

| Compound | $R_{38}$ | Q |
|---|---|---|
| 224 | $OCOCH_3$ | $CH_2CONHNH_2$ |
| 225 | $OCOCH_3$ | $CH_2CON\text{(4-methylpiperidinyl)}$ |

TABLE IX-continued

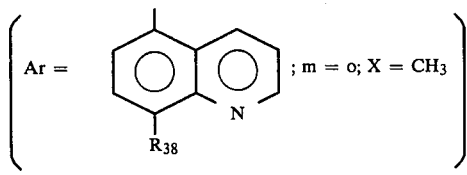

$$\left( Ar = \underset{R_{38}}{\text{[structure]}} ; m = o; X = CH_3 \right)$$

| Compound | R38 | Q |
|---|---|---|
| 226 | OCONHCH3 | CH2CON(CH3)CO—C6H5 |
| 227 | OCOC2H5 | CH2CH2CH2CON(C6H5)NH2 |
| 228 | OCOCH2Cl | CH2CH2COOH |
| 229 | OCONHC2H5 | CH2–<(O,O) [dioxolane] |
| 230 | OCONHC3H7(i) | CH(CH3)–C<(O,O) |
| 231 | OCONHC4H9(n) | CH(C4H9(n))CONHNH2 |

FORMULATION EXAMPLES

EXAMPLE 7

Dusts: The following substances are used to formulate (a) 5% and (b) a 2% dust:
(a) 5 parts of active substance, 95 parts of talc;
(b) 2 parts of active substance, 1 part of highly dispersed silicic acid, 97 parts of talc.

The active substances are mixed with the carriers and ground and in this form can be processed to dusts for application.

EXAMPLE 8

Granulate: The following substances are used to formulate a 5% granulate:
5 parts of active substance
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE 9

Wettable powders: The following constituents are used to formulate (a) a 70%, (b) a 40%, (c) and (d) a 25% and (e) a 10% wettable powder:

(a)
70 parts of active substance
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk (b)
40 parts of active substance
5 parts of sodium ligninsulfonate
1 parts of sodium dibutylnaphthalenesulfonic acid
54 parts of silicic acid (c)
25 parts of active substance
4.5 parts of calcium ligninsulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminum silicate
16.5 parts of kieselguhr
46 parts of kaolin (e)
10 parts of active substance
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

EXAMPLE 10

Emulsifiable concentrate: The following substances are used to formulate a 25% emulsifiable concentrate:
25 parts of active substance
2.5 parts of epoxidised vegetable oil
10 parts of an alkylarylsulfonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

BIOLOGICAL EXAMPLES

EXAMPLE 11

Pre-emergence antidote test (basic test)

General test method: Small flower pots (diameter 6 cm at the top) are filled with garden soil into which the plant seed is sown, covered with the soil and gently pressed firm. Then the antidote is sprayed as test substance in the form of a dilute solution (obtained from a wettable powder) in an amount corresponding to 4 kg/ha. the herbicide is sprayed onto the soil directly afterwards in corresponding amount. After the pots have stood for 18 days at about 20°–23° C. and 60°–70° C. relative humidity, evaluation is made in accordance with a linear scale from 1 (denoting total damage to the plant) to 9 (denoting undamaged healthy plant). Plants without antidote protection are used as control.

The following herbicides and plants were employed:
(1) 1.5 kg/ha of α-[4-(p-trifluoromethylphenoxy)-phenoxy]-propionic acid n-butoxyethyl ester in maize of the "Orla 264" variety.

(2) 1.5 kg/ha of Metolachlor=N-(-1-methyl-2-methoxyethyl)-N-chloroacetyl-2-ethyl-6-methylaniline in sorghum of the "Funk G-522" variety.
(3) 2 kg/ha of Prometryn=2,4-bis(isopropylamino)-6-methylthio-s-triazine in soybeans.
(4) 2 kg/ha of 4-ethylamino-6-tert-butylamino-2-chloro-s-triazine in wheat of the "Farnese" variety.
(5) 4 kg/ha of Prometryn=2,4-bis(isopropylamino)-6-methylthio-s-triazine in sorghum of the "Funk G-522" variety.
(6) 2 kg/ha of α-[4-(p-trifluoromethylphenoxy)-phenoxy]-propionic acid n-butoxyethyl ester in barley of the "Mazurka" variety.

A good antidote action is obtained in these tests with the compounds of the formula I. The results are e.g. as follows:

| Test variant | Compound | Rating of the herbicidal action (with/without antidote) |
|---|---|---|
| 5 | 37 | 5/8 |
| 5 | 41 | 4/7 |
| 5 | 42 | 4/6 |
| 5 | 43 | 4/7 |
| 6 | 40 | 3/7 |
| 6 | 84 | 5/7 |

EXAMPLE 12

Antidote action on separate application (antidote/pre-emergence, herbicide/post-emergence)

General test method:

Small flower pots (diameter 6 cm at the top) are filled with sandy loam into which the plant is sown. After covering the seed, a dilute solution of the antidote as test substance is sprayed onto the surface of the soil in an amount corresponding to 4 kg/ha. The pots are kept at 20°–23° C. and 60°–70° C. relative humidity. When the plants have attained the 2- to 3-leaf stage after 10 days, they are treated as indicated below with the corresponding amount of herbicide. Evaluation is made 14 days after the application of the herbicide, using the same rating system as in Example 11. Plants unprotected by antidote are used as control.

The herbicides and plants employed are:
(1) 4 kg/ha of Ametryn=2-ethylamino-4-isopropylamino-6-methylthio-s-triazine in maize of the "Orla 264" variety.
(2) 1 kg/ha of Prometryn=2,4-bis(isopropylamino)-6-methylthio-s-triazine in sorghum of the "Funk G-522" variety.
(3) 0.25 kg/ha of α-[4-(p-trifluoromethylphenoxy)-phenoxy]-propionic acid n-butoxyethyl ester in barley of the "Mazurka" variety.

A good antidote action was obtained in these tests with compounds of the formula (I).

EXAMPLE 13

Antidote action in transplanted rice on separate application (antidote/pre-emergence, herbicide/post-emergence)

Plastic tubs measuring 8×8×10 cm are filled with wet marshy soil to 2 cm below the edge. A dilute solution of the antidote as test substance is sprayed onto the surface of the soil in an amount corresponding to 4 kg/ha. Rice plants of the "IR-88" variety are transplanted in the 1½- to 2-leaf stage into the prepared tubs. On the next day, the water level is raised to about 1.5 cm. Four days after transplantation, 2-ethylamino-4-(1,2-dimethyl-n-propylamino)-6-methylthio-s-triazine is added to the water in granule form in an amount corresponding to 0.75 kg/ha. During the test, the temperature is 26°–28° C. and the relative humidity 60°–80° C. Evaluation is made 20 days after the treatment with herbicide, using the same rating as in Example 11. Plants not protected with antidote are used as control. A good antidote action is obtained in this test with compounds of the formula I.

| Compound | Rating of the herbicidal action (without/with antidote) |
|---|---|
| 40 | 2/4 |
| 3 | 2/6 |
| 41 | 4/7 |
| 42 | 4/8 |
| 10 | 5/8 |
| 58 | 5/7 |
| 60 | 3/6 |

EXAMPLE 14

Pre-emergence antidote test in nutrient solution

A Hewitt nutrient solution, which contains the amount of herbicide indicated below as well as 10 ppm of the antidote to be tested, is prepared.

Seeds which would normally be damaged in the indicated test concentrations of the herbicide employed are sown in granular zonolith (expanded vermiculite) in plastic flower pots (diameter 6 cm at the top) which are perforated at the bottom. Each pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid is daily replenished to 50 ml with pure Hewitt nutrient solution. Evaluation is made 3 weeks after the start of the test, using the same rating as in Example 8. The control solution employed in the parallel test contains no antidote.

The herbicides and plants employed are:
(1) 4 ppm of Prometryn=2,4-bis(isopropylamino)-6-methylthio-s-triazine in sorghum of the "Funk G-522" variety.
(2) 4 ppm of 4-ethylamino-6-tert-butylamino-2-chloro-s-triazine in wheat of the "Farnese" variety.
(3) 4 ppm of α-[4-(p-trifluoromethylphenoxy)-phenoxy]-propionic acid n-butoxyethyl ester in barley of the "Mazurka" variety.
(4) 5 ppm of Metolachlor=N-(1-methyl-2-methoxyethyl)-N-chloroacetyl-2-ethyl-6-methaniline in sorghum of the "Funk G-522" variety.

A good antidote action is obtained with the compounds of the formula I. The results are e.g. as follows:

| Test variant | Compound | Rating of the herbicidal action with/without antidote |
|---|---|---|
| 1 | 54 | 3/6 |
| 3 | 85 | 3/6 |
| 4 | 3 | 4/7 |
| 4 | 11 | 2/6 |
| 4 | 40 | 4/7 |
| 4 | 41 | 4/7 |

-continued

| Test variant | Compound | Rating of the herbicidal action with/without antidote |
| --- | --- | --- |
| 4 | 42 | 4/7 |
| 4 | 53 | 3/7 |
| 4 | 54 | 3/8 |
| 4 | 55 | 3/8 |

EXAMPLE 15

Pre-emergence antidote test in nutrient solution (rice)

A Hewitt nutrient solution, which additionally contains 10 ppm of the antidote to be tested, is prepared.

Rice seeds of the "IR-8" variety are sown in granular filling material (granular zonolith) in plastic flower pots (diameter 6 cm at the top) which are perforated at the bottom. Each pot is then placed in a second transparent plastic flower pot (diameter 7 cm at the top) which contains about 50 ml of the nutrient solution prepared from herbicide and antidote. This nutrient solution then rises by capillary action in the filling material of the smaller pot and moistens seed and plant. The loss in fluid is daily replenished to 50 ml with pure Hewitt solution. After 15 days, the rice plants are transplanted in the 2- to 2½-leaf stage in rectangular plastic pots (8×8×10 cm) which are filled with 500 ml of wet, marshy soil. The water level is increased next day to 1-2 cm above the level of the soil. Four days after transplantation, the herbicide 2-ethylamino-4-(1,2-dimethyl-n-propylamino)-6-methylthio-s-triazine is added in granule form in an amount corresponding to 0.75 kg/ha. Evaluation is made 3 weeks later in accordance with the rating employed in Example 11 and subsequent Examples. The control solution used in the parallel test contains no antidote. A good antidote action was obtained in this test with the compounds of the formula (I).

The results are e.g. as follows:

| Compound | Herbicidal action without/with antidote |
| --- | --- |
| 21 | 1/7 |
| 87 | 2/6 |
| 86 | 5/6 |

EXAMPLE 16

Post-emergence antidote test in nutrient solution

General test method:

Small plastic flower pots (diameter 6 cm at the top), which are perforated at the bottom, are filled with granular zonolith and the seeds are sown in this material. Each pot is then placed in a second transparent plastic flower pot (diameter 7 cm at the top) which contains 50 ml of water which rises by capillary action and moistens the seed. Form the 5th day, the continual loss in water is made up with Hewitt nutrient solution. From the 15th day, when the plant is in the 1½-2-leaf stage, 10 ppm of the antidote to be tested and the amount of herbicide indicated below are added to the nutrient solution which has again been replenished to 50 ml. From the 16th day, the loss in fluid is again made up with pure Hewitt nutrient solution. During the entire duration of the test, the temperature is 20°-23° C. and the relative humidity 60°-70%. Evaluation is made 3 weeks after the addition of the herbicide in accordance with the rating employed in Example 11 and subsequent Examples.

Test variants:

(1) 15 ppm of α-[4-(3,5-dichloropyridyl-2-oxy)-phenoxy]-propionic acid propargylthiolo-ester in wheat of the "Zenith" variety.

(2) 4 ppm of 4-ethylamino-6-tert-butylamino-2-chloro-s-triazine in wheat of the "Zenith" variety.

(3) 2 ppm of α-[4-(p-trifluoromethylphenoxy)-phenoxy]-propionic acid n-butoxyethyl ester in maize of the "Orla" variety.

(4) 8 ppm of α-[4-(p-trifluoromethylphenoxy)-phenoxy]-propionic acid n-butoxyethyl ester in sorghum of the "Funk G-522" variety.

(5) 4 ppm of Prometryn=2,4-bis(isopropylamino)-6-methylthio-s-triazine in sorghum of the "Funk G-522" variety.

(6) 8 ppm of α-[4-(3,5-dichloropyridyl-2-oxy)-phenoxy]-propionic acid methyl ester in wheat of the "Zenith" variety.

A good antidote action is obtained in these tests with compounds of the formula (I).

EXAMPLE 17

Antidote test—seed soaking

Rice seeds of the "IR-8" variety are immersed for 48 hours in solutions of the test substances in concentrations of 10, 100 or 1000 ppm. The seeds are then allowed to dry for about 2 hours until they are no longer tacky. Rectangular plastic tubs (8×8×10 cm) are filled with sandy loam to 2 cm below the edge. 4 g of seeds are sown in each tub and only very loosely covered (to about the diameter of the seed). The soil is kept in a moist (non-marshy) state. Then a dilute solution of the herbicide N-(1-methyl-2-methoxyethyl)-N-chloroacetyl-2-ethyl-6-methylaniline is applied in an amount corresponding to 1.5 kg/ha. Evaluation is made 7 and 18 days after transplantation in accordance with the rating employed in Example 11 and subsequent Examples. A good antidote action is obtained in this test with compounds of the formula (I), in particular with compounds 3, 8, 10, 37, 40 and 50.

EXAMPLE 18

Antidote test (root dipping)

Rice plants of the "IR-8" variety are reared in soil until they are in the 1½- to 2-leaf stage and then superficially washed. Then only the roots of the plants, in bunches, are dipped for 45 minutes in a dish containing solutions of the test substance in a concentration of 10, 100 or 1000 ppm. The plants are then transplanted in sandy loam in containers measuring 47×29×24 cm. The surface of the soil is covered with water to a height of 1½ to 2 cm. One day after transplantation, a dilute solution of the herbicide N-n-propoxyethyl-N-chloroacetyl-2,6-diethylaniline is pipetted directly into the water in an amount corresponding to 1.5 kg/ha. Evaluation is made 7 and 18 days after transplantation in accordance with the rating employed in Example 11 and subsequent Examples. Good antidote action is obtained in this test with compounds of the formula (I).

EXAMPLE 19

In a field planted with soybeans (Lee 68 variety), aqueous active substance spray mixtures were applied to parcels measuring 2.5×10 m in amounts corresponding to rates of application of 0.5, 1 and 2 kg/ha. At the time of application, the soybean plants were in the 8- to 10-leaf stage. Untreated parcels acted as control. At harvesting time, 15 weeks after application, the average growth in height was determined for each parcel and the yield of harvested beans was weighed.

At rates of application of 1 and 2 kg, an approximately 15–20% smaller growth in height compared with the control was obtained with compound 41, while the yield had increased by 17 to 24%.

What is claimed is:

1. A method for increasing the yield in crops of soy beans, which comprises applying thereto an effective amount of phenylacetonitrile oxime-(2'-ethylenedioxyethyl) ether.

2. A method for increasing the yield in crops of soy beans, which comprises applying thereto an effective amount of phenylacetonitrile oxime-(2'-propylenedioxyethyl) ether.

3. A method for increasing the yield in crops of soy beans, which comprises applying thereto an effective amount of 2-chlorophenylacetonitrile oxime-[2'-(2",2"-dimethylpropylenedioxy)-ethyl] ether.

* * * * *